(12) United States Patent
Jawahar et al.

(10) Patent No.: US 12,046,356 B2
(45) Date of Patent: Jul. 23, 2024

(54) SYSTEM AND METHOD OF SCRIBBLE BASED SEGMENTATION FOR MEDICAL IMAGING USING MACHINE LEARNING

(71) Applicants: International Institute of Information Technology, Hyderabad, Hyderabad (IN); Indian Institute of Technology, Delhi, New Delhi (IN)

(72) Inventors: C. V. Jawahar, Hyderabad (IN); Bhavani Sambaturu, Hyderabad (IN); Ashutosh Gupta, New Delhi (IN); Chetan Arora, Hari Nagar (IN)

( * ) Notice: Subject to any disclaimer, the term of this patent is extended or adjusted under 35 U.S.C. 154(b) by 373 days.

(21) Appl. No.: 17/579,435

(22) Filed: Jan. 19, 2022

(65) Prior Publication Data

US 2022/0230733 A1 Jul. 21, 2022

(30) Foreign Application Priority Data

Jan. 19, 2021 (IN) .............................. 202141002488

(51) Int. Cl.
*G16H 30/40* (2018.01)
*G06T 7/00* (2017.01)
*G06T 7/10* (2017.01)
*G16H 50/20* (2018.01)

(52) U.S. Cl.
CPC .......... *G16H 30/40* (2018.01); *G06T 7/0012* (2013.01); *G06T 7/10* (2017.01); *G16H 50/20* (2018.01); *G06T 2200/24* (2013.01); *G06T 2207/20081* (2013.01); *G06T 2207/30008* (2013.01); *G06T 2207/30024* (2013.01); *G06T 2207/30096* (2013.01)

(58) Field of Classification Search
CPC .......... G16H 30/40; G16H 50/20; G06T 7/10; G06T 7/0012; G06T 2200/24; G06T 2207/20081; G06T 2207/30008; G06T 2207/30024; G06T 2207/30096
USPC ...................................................... 382/128
See application file for complete search history.

(56) References Cited

U.S. PATENT DOCUMENTS

2022/0277540 A1* 9/2022 Jawahar ................. G06V 10/26

* cited by examiner

*Primary Examiner* — Michael R Neff (57) ABSTRACT

A system and method generating an optimized medical image using a machine learning model are provided. The method includes (i) receiving one or more medical images, (ii) segmenting to generate a transformed medical image for detecting a plurality of target elements, (iii) displaying the transformed medical image, (iv) receiving markings and scribblings associated with scribble locations from a user, (v) identifying errors associated with an outline of a target element, (vi) computing a loss function for a location of pixels where the target element is located on the transformed medical image, (vii) modifying the pre-defined weights (w) to match the segmentation output and the determined target element, (viii) determining whether the segmentation output is matched with the target element and (ix) generating the optimized medical image if the segmentation output is matched with the determined target element.

19 Claims, 8 Drawing Sheets

```
┌─────────────────────────────────────────────┐
│ RECEIVING ONE OR MORE MEDICAL IMAGES FROM   │
│ AT LEAST ONE OF A CLOUD, A USER DEVICE OR   │
│ A MEDICAL DEVICE                            │
│                    502                      │
└─────────────────────────────────────────────┘
                      ▼
┌─────────────────────────────────────────────┐
│ SEGMENTING, USING THE MACHINE LEARNING      │
│ MODEL, A RECEIVED MEDICAL IMAGE TO GENERATE │
│ A TRANSFORMED MEDICAL IMAGE FOR DETECTING   │
│ A PLURALITY OF TARGET ELEMENTS              │
│                    504                      │
└─────────────────────────────────────────────┘
                      ▼
┌─────────────────────────────────────────────┐
│ DISPLAYING, USING A GRAPHICAL USER          │
│ INTERFACE, THE TRANSFORMED MEDICAL IMAGE    │
│ WHICH SPECIFIES THE PLURALITY OF TARGET     │
│ ELEMENTS ON THE MEDICAL IMAGE WITH OUTLINES │
│                    506                      │
└─────────────────────────────────────────────┘
                      ▼
┌─────────────────────────────────────────────┐
│ ENABLING A USER TO MARK OR SCRIBBLE ON THE  │
│ TRANSFORMED MEDICAL IMAGE TO DETERMINE A    │
│ TARGET ELEMENT ON THE TRANSFORMED MEDICAL   │
│ IMAGE                                       │
│                    508                      │
└─────────────────────────────────────────────┘
                      ▼
┌─────────────────────────────────────────────┐
│ RECEIVING THE TRANSFORMED MEDICAL IMAGE     │
│ THAT IS MARKED OR SCRIBBLED BY THE USER TO  │
│ IDENTIFY ERRORS ASSOCIATED WITH AN OUTLINE  │
│ OF THE TARGET ELEMENT ON THE TRANSFORMED    │
│ MEDICAL IMAGE BASED ON MARKINGS AND         │
│ SCRIBBLINGS RECEIVED FROM THE USER, USING   │
│ THE MACHINE LEARNING MODEL                  │
│                    510                      │
└─────────────────────────────────────────────┘
```

SYSTEM AND METHOD OF SCRIBBLE BASED SEGMENTATION FOR MEDICAL IMAGING USING MACHINE LEARNING

CROSS-REFERENCE TO PRIOR-FILED PATENT APPLICATIONS

This application claims priority from the Indian provisional application no. 202141002488 filed on Jan. 19, 2021, which is herein incorporated by reference.

TECHNICAL FIELD

The embodiments herein generally relate to a medical image segmentation model, and more particularly, to a system and method for generating a scribble-based segmentation for medical imaging using a machine learning model.

DESCRIPTION OF RELATED ART

In this modern era, many diagnosis methods are introduced in order to treat both external and internal injuries or diseases. The study of diagnosing and treating injuries or diseases using medical imaging is known as Radiology. Radiologists analyze the diagnosis reports or medical images like X-rays, computed tomography (CT), magnetic resonance imaging (MRI), nuclear medicine, positron emission tomography (PET), and ultrasound images manually on daily basis. Identifying and reviewing a part of the body specified in the respective medical image is a mandatory task for a medical practitioner before suggesting the treatment procedures to a patient.

Image segmentation has been evolved such that some techniques are capable of identifying and differentiating several features from an image. In the case of medical imaging, these techniques cannot work efficiently as expected. A target element of respective medical imaging in the body is not identified. The existing systems face a major problem in identifying the correct outline and shape of the target element from the provided medical imaging. Sometimes, the shape of the target element identified may be improper or blurry in nature. It may not be proper guidance for the medical practitioner in the diagnosis.

Therefore, there arises a need to address the aforementioned technical drawbacks in existing technologies to generate a segmentation model for medical imaging.

SUMMARY

In view of the foregoing, an embodiment herein provides a system for generating an optimized medical image using a machine learning model. The system includes a memory and a processor. The processor is configured to (i) receive one or more medical images from at least one of a cloud, a user device or a medical device, (ii) segment, using the machine learning model, a received medical image to generate a transformed medical image for detecting one or more target elements, (iii) display, using a graphical user interface, the transformed medical image which specifies the one or more target elements on the medical image with outlines, (iv) enable a user to mark or scribble on the transformed medical image to determine a target element on the transformed medical image, (v) receive the transformed medical image that is marked or scribbled by the user to identify errors associated with an outline of the target element on the transformed medical image based on markings and scribblings received from the user using the machine learning model, (vi) compute, using the machine learning model, a loss function for a location of pixels where the target element is located on the transformed medical image, (vii) match the segmentation output and the target element at the scribble locations by modifying, using the machine learning model, the pre-defined weights (w) based on a derivative of the loss function with respect to the pre-defined weights (w) which is weighted by a learning rate, (viii) determine, using the machine learning model, whether the segmentation output is matched with the target element on the transformed medical image and (ix) generate the optimized medical image if the segmentation output is matched with the target element on the transformed medical image. The transformed medical image is a segmented output that is generated based on pre-defined weights (w). The transformed medical image is generated by the machine learning model that generates the outlines on the one or more target elements. The learning rate determines a speed of change the pre-defined weights.

In some embodiments, the pre-defined weights (w) are modified to reduce a value of the loss function. The value of the loss function is decreased when the segmentation output is matched with the target element at the scribble locations. The value of the loss function is increased when the segmentation output is not matched with the target element at the scribble locations.

In some embodiments, the system includes a stochastic gradient descent process that modifies the pre-defined weights (w) optimally to reduce the loss function. The derivative of the loss function is computed with respect to the pre-defined weights (w). The pre-defined weights (w) are modified using a weighted multiplication of the learning rate and the derivative of the loss function.

In some embodiments, the processor is configured to receive the markings and scribblings from the user over a missed-out area of one or more detected elements from an initial outlined target element through a graphical user interface.

In some embodiments, the processor is configured to receive the markings and scribblings from the user over the missed-out area of the one or more target elements determined from the optimized medical image using the graphical user interface and optimizes based on the markings and scribblings received from the user.

In some embodiments, the processor is configured to (a) provide optimized medical images and corresponding (i) pre-defined weights and (ii) the markings and scribblings received from the user to the machine learning model as input data and (b) train the machine learning model using the input data to generate a trained machine learning model to generate the optimized medical image.

In some embodiments, the one or more target elements include at least one of a cell, a ligament, a tissue, an organ, a tumor, a lesion, a part of bone, or an accessory bone.

In another aspect, a method for generating an optimized medical image using a machine learning model is provided. The method includes (i) receiving one or more medical images from at least one of a cloud, a user device or a medical device, (ii) segmenting, using the machine learning model, a received medical image to generate a transformed medical image for detecting one or more target elements, (iii) displaying, using a graphical user interface, the transformed medical image which specifies the one or more target elements on the medical image with outlines, (iv) enabling a user to mark or scribble on the transformed medical image to determine a target element on the transformed medical image, (v) receiving the transformed medical image that is marked or scribbled by the user to identify errors associated with an outline of the target element on the transformed medical image based on markings and scribblings received from the user, using the machine learning model, (vi) computing, using the machine learning model, a loss function for a location of pixels where the target element is located on the transformed medical image, (vii) matching the segmentation output and the target element at the scribble locations by modifying, using the machine learning model, the pre-defined weights (w) based on a derivative of the loss function with respect to the pre-defined weights (w) which is weighted by a learning rate, (viii) determining, using the machine learning model, whether the segmentation output is matched with the target element on the transformed medical image, (ix) generating the optimized medical image if the segmentation output is matched with the target element on the transformed medical image. The transformed medical image is a segmented output that is generated based on pre-defined weights (w). The transformed medical image is generated by the machine learning model that generates the outlines on the one or more target elements. The learning rate determines a speed of change the pre-defined weights.

In some embodiments, the pre-defined weights (w) are modified to reduce a value of the loss function. The value of the loss function is decreased when the segmentation output is matched with the target element at the scribble locations. The value of the loss function is increased when the segmentation output is not matched with the target element at the scribble locations.

In some embodiments, the method includes a stochastic gradient descent process. The stochastic gradient descent process includes modifying the pre-defined weights (w) optimally to reduce the loss function. The derivative of the loss function is computed with respect to the pre-defined weights (w). The pre-defined weights (w) are modified using a weighted multiplication of the learning rate and the derivative of the loss function.

In some embodiments, the method includes receiving the markings and scribblings from the user over a missed-out area of one or more detected elements from an initial outlined target element through a graphical user interface.

In some embodiments, the method includes receiving the markings and scribblings from the user over the missed-out area of the one or more target elements determined from the optimized medical image using the graphical user interface and optimizes based on the markings and scribblings received from the user.

In another aspect, a non-transitory program storage device readable by a computer, and including a program of instructions executable by the computer to perform a method for generating an optimized medical image using a machine learning model is provided. The method includes (i) receiving one or more medical images from at least one of a cloud, a user device or a medical device, (ii) segmenting, using the machine learning model, a received medical image to generate a transformed medical image for detecting one or more target elements, (iii) displaying, using a graphical user interface, the transformed medical image which specifies the one or more target elements on the medical image with outlines, (iv) enabling a user to mark or scribble on the transformed medical image to determine a target element on the transformed medical image, (v) receiving the transformed medical image that is marked or scribbled by the user to identify errors associated with an outline of the target element on the transformed medical image based on markings and scribblings received from the user, using the machine learning model, (vi) computing, using the machine learning model, a loss function for a location of pixels where the target element is located on the transformed medical image, (vii) matching the segmentation output and the target element at the scribble locations by modifying, using the machine learning model, the pre-defined weights (w) based on a derivative of the loss function with respect to the pre-defined weights (w) which is weighted by a learning rate, (viii) determining, using the machine learning model, whether the segmentation output is matched with the target element on the transformed medical image, (ix) generating the optimized medical image if the segmentation output is matched with the target element on the transformed medical image. The transformed medical image is a segmented output that is generated based on pre-defined weights (w). The transformed medical image is generated by the machine learning model that generates the outlines on the one or more target elements. The learning rate determines a speed of change the pre-defined weights In some embodiments, the pre-defined weights (w) are modified to reduce a value of the loss function. The value of the loss function is decreased when the segmentation output is matched with the target element at the scribble locations. The value of the loss function is increased when the segmentation output is not matched with the target element at the scribble locations.

In some embodiments, the method includes a stochastic gradient descent process. The stochastic gradient descent process includes modifying the pre-defined weights (w) optimally to reduce the loss function. The derivative of the loss function is computed with respect to the pre-defined weights (w). The pre-defined weights (w) are modified using a weighted multiplication of the learning rate and the derivative of the loss function.

In some embodiments, the method includes receiving the markings and scribblings from the user over a missed-out area of one or more detected elements from an initial outlined target element through a graphical user interface.

In some embodiments, the method includes receiving the markings and scribblings from the user over the missed-out area of the one or more target elements determined from the optimized medical image using the graphical user interface and optimizes based on the markings and scribblings received from the user.

In some embodiments, the method includes (a) providing optimized medical images and corresponding (i) pre-defined weights and (ii) markings and scribblings received from the user to the machine learning model as input data, (b) training the machine learning model using the input data to generate a trained machine learning model to generate the optimized medical image.

The system and method of scribble-based smart segmentation model for medical imaging using machine learning provide efficient results than existing systems using human or domain expert interaction to obtain more accurate results. This system helps in reducing the human effort of radiologists during reviewing the medical images with precise identification and detection of target elements using any fully automated deep learning-based image segmentation.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF THE DRAWINGS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there is a need for a system and method for generating a scribble-based segmentation for medical imaging using a machine learning model. Referring now to the drawings, and more particularly to FIG. 1 through FIG. 6, where similar reference characters denote corresponding features consistently throughout the figures, preferred embodiments are shown.

Figure 1:
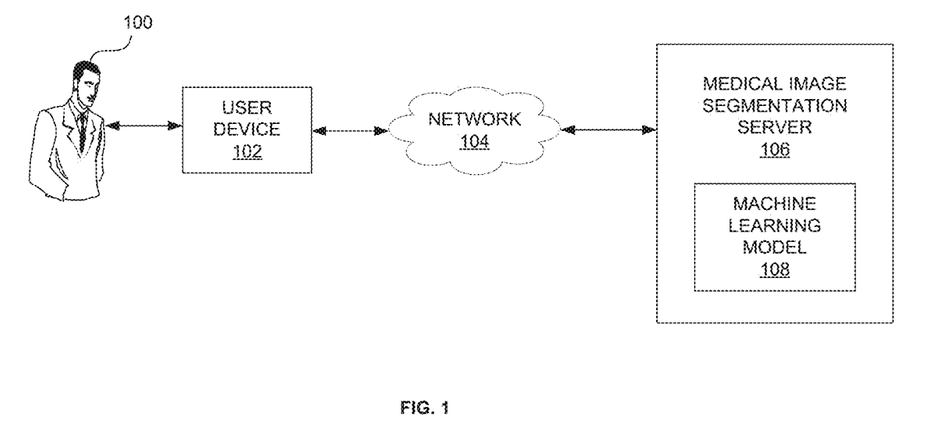
FIG. 1 illustrates a system for generating a scribble-based segmentation for medical imaging, according to some embodiments herein.

FIG. 1 illustrates a system for generating a scribble-based segmentation for medical imaging, according to some embodiments herein. The system includes a user 100, a user device 102, a network 104, a medical image segmentation server 106, a machine learning model 108. The user device 102 receives one or more medical images as inputs from the user 100. In some embodiments, the device may be, but not limited to a mobile phone, a tablet, a Personal computer or a laptop. In some embodiments, medical images may include, but are not limited to, X-rays, computed tomography (CT), magnetic resonance imaging (MRI), nuclear medicine, positron emission tomography (PET), and ultrasound images.

The medical image segmentation server 106 receives the one or more medical images through a network 104. In some embodiments, the network 104 may be a wireless network or a wired network. The medical image segmentation server 106 segments received one or more medical images. The medical image segmentation server 106 detects one or more target elements from segmented one or more medical images using a machine learning model 108. In some embodiments, the one or more target elements may include one or more, but not limited to, some pathological objects may be a cell, a ligament, a tissue, an organ, a tumor, a lesion, a part of bone or an accessory bone. The medical image segmentation server 106 generates an outline on the one or more target elements to specify the one or more target elements. In some embodiments, the machine learning model 108 may be, but not limited to any of, without modifying or updating, a deep learning based fully automated image segmentation model that is already existing without any need to change an architecture of the system and method that is being implemented presently.

In some embodiments, the medical image segmentation server 106 makes a new ground truth as the accuracy is increased by using this method and the machine learning model 108. The medical image segmentation server 106 displays an outlined target element to the user 100 through a user interface in the user device 102. In some embodiments, at least one of the target elements may be completely missed out. In some embodiments, the outlined target element may not show the target element completely without any errors in outlines. The user 100 checks the outlined target element for an error or an incorrect outline marking through the user interface in the user device 102. The user interface in the user device 102 allows the user 100 to scribble the missed-out area of the one or more target elements from the outlined target element. In some embodiments, the user 100 is allowed to scribble or mark the missed-out area in form of, any of, but not limited to, a point or a scribble or a box that is a rectangle or a square-shaped box.

The medical image segmentation server 106 receives a marking or a scribbling over a missed-out area of the one or more detected elements from an initial outlined target element through the user interface in the user device 102. In some embodiments, there may be one or more markings or scribblings over the one or more target elements. In some embodiments, the machine learning model 108 need not be necessarily get pre-trained by any specific data set, rather the machine learning model 108 gets trained while processing the user-provided scribblings or markings alone. The medical image segmentation server 106 optimizes the initial outlined target element based on the markings or scribblings received through the user interface in the user device 102, The medical image segmentation server 106 trains the machine learning model 108 with the markings or scribblings used to optimize the outlined target element. The medical image segmentation server 106 generates an optimized medical image based on one or more learnings from the trained machine learning model 108 and the markings and scribblings received from the user 100 through the user interface in the user device 102.

The medical image segmentation server 106 displays the optimized medical image to the user 100 through the user interface in the user device 102. In some embodiments, the generated optimized medical image may not show the one or more target elements completely without any errors in outlines. The user 100 examines displayed optimized medical image and checks for any error or an incorrect outline marking using the user interface in the user device 102. The user interface in the user device 102 allows the user 100 to scribble again the missed-out area of the one or more target elements from the optimized medical image. The medical image segmentation server 106 receives a marking or a scribbling over the missed-out area of the one or more target elements from the optimized medical image from the user interface in the user device 102 and again optimizes based on the received scribblings and markings. The medical image segmentation server 106 again trains the machine learning model 108 with optimized medical images from the learnings of the ML module and the scribblings.

The medical image segmentation server 106 generates an optimized medical image based on one or more new learnings from the trained machine learning model 108 and the markings and scribblings received from the user 100 through the user interface in the user device 102. The medical image segmentation server 106 displays the optimized medical image to the user 100 through the user interface in the user device 102. The medical image segmentation server 106 repeats the examining, and generates the new optimized medical images until a well-optimized medical image with correct outlines of one or more detected elements is obtained. In some embodiments, the medical image segmentation server 106 may optimize the medical images several times.

Figure 2:
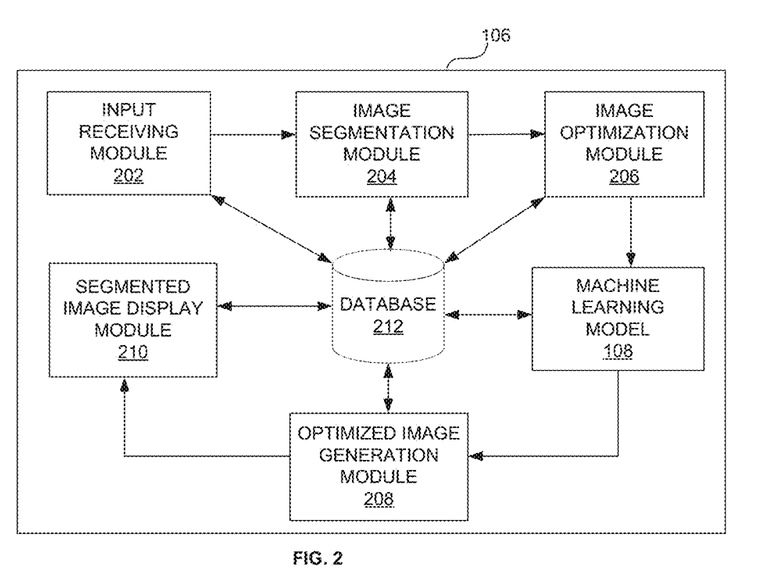
FIG. 2 is an exploded view of a medical image segmentation server of FIG. 1, according to some embodiments herein.

FIG. 2 is an exploded view of medical image segmentation server 106 of FIG. 1, according to some embodiments herein. The exploded view of medical image segmentation server 106 includes, an input receiving module 202, an image segmentation module 204, an image optimization module 206, a machine learning model 108, an optimized image generation module 208, a segmented medical image display module 210, and a database 212. The input receiving module 202 receives one or more medical images as inputs from the user through the user device 102.

The input receiving module 202 receives the medical images from the user device 102 through the network 104. The image segmentation module 204 segments received one or more medical images. The image optimization module 206 detects one or more target elements from segmented one or more medical images using the machine learning model 108. In some embodiments, the detected elements may include one or more, but not limited to, some pathological objects like a cell, a ligament, a tissue, an organ, a tumor, a lesion, a part of bone or an accessory bone. The optimized image generation module 208 generates an outline on the one or more target elements to specify the one or more target elements. In some embodiments, the machine learning model 108 may be any, but not limited to fully automated deep-learning based image segmentation.

The segmented image display module 210 displays an outlined target element to the user 100 through a user interface in the user device 102. In some embodiments, the generated initial segmented image may not show the detected element completely without any errors in outlines. The user 100 checks the outlined target element for an error or an incorrect outline marking through the user interface in the user device 102. The user interface in the user device 102 allows the user 100 to scribble the missed-out area of the one or more target elements from the outlined target element. The input receiving module 202 receives a marking or a scribbling over a missed-out area of the one or more detected elements from the initial segmented image through the user interface in the user device 102. The image optimization module 206 receives a marking or a scribbling over the missed-out area of the one or more detected elements from an initial outlined target element from the input receiving module 202 through the database 212. In some embodiments, there may be one or more markings or scribblings over the one or more target elements. The image optimization module 206 optimizes an initial outlined target element based on the markings or scribblings received through the user interface in the user device 102. The image optimization module 206 trains the machine learning model 108 with the markings or scribblings used to optimize the outlined target element.

The optimized image generation module 208 generates an optimized medical image based on one or more learnings from the trained machine learning model 108 and the markings and scribblings received from the user 100 through the user interface in the user device 102. The segmented image display module 210 displays the optimized medical image to the user 100 through the user interface in the user device 102. In some embodiments, the generated optimized medical image may not show the one or more target elements completely without any errors in outlines. The user 100 examines displayed optimized medical image and checks for any error or an incorrect outline marking using the user interface in the user device 102. The medical image segmentation server 106 repeats the examining, and generates the new optimized medical images until a well-optimized medical image with correct outlines of one or more detected elements is obtained. In some embodiments, the medical image segmentation server 106 may optimize the medical images several times.

Figure 3:
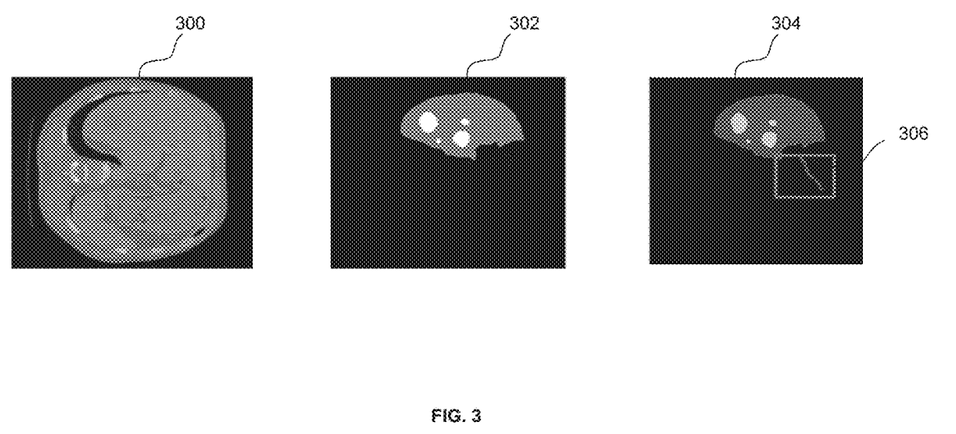
FIG. 3 illustrates an exemplary representation of a segmented image, an optimized image, and scribbled images, according to some embodiments herein.

FIG. 3 illustrates an exemplary representation of a set of segmented, optimized, and scribbled medical images, according to some embodiments herein. The exemplary representation of a set of segmented, optimized, and scribbled medical images includes, a medical image 300, an initial segmented image 302, a scribbled image 304, and scribbling or marking 306. The medical image 300 is the exemplary representation of the input medical image received by the input receiving module 202 from the user device 102. The initial segmented image 302 is the exemplary representation of the initial segmented image generated by the image segmentation module 204 from medical image segmentation server 106. The segmented medical image display module 210 displays the initial segmented image 302 to the user 100 through the user device 102. The scribbling or marking 306 is the exemplary representation of the scribblings or markings provided by the user 100 through user device 102 using the user interface of the user device 102. In some embodiments, the scribblings or markings may be one or more on one or more detected elements of the medical image 300. The scribbled image 304 is the exemplary representation of the displaying segmented medical image after the user 100 provides the scribbling or marking over the missed-out area of the one or more detected elements of medical image 300.

Figure 4A:
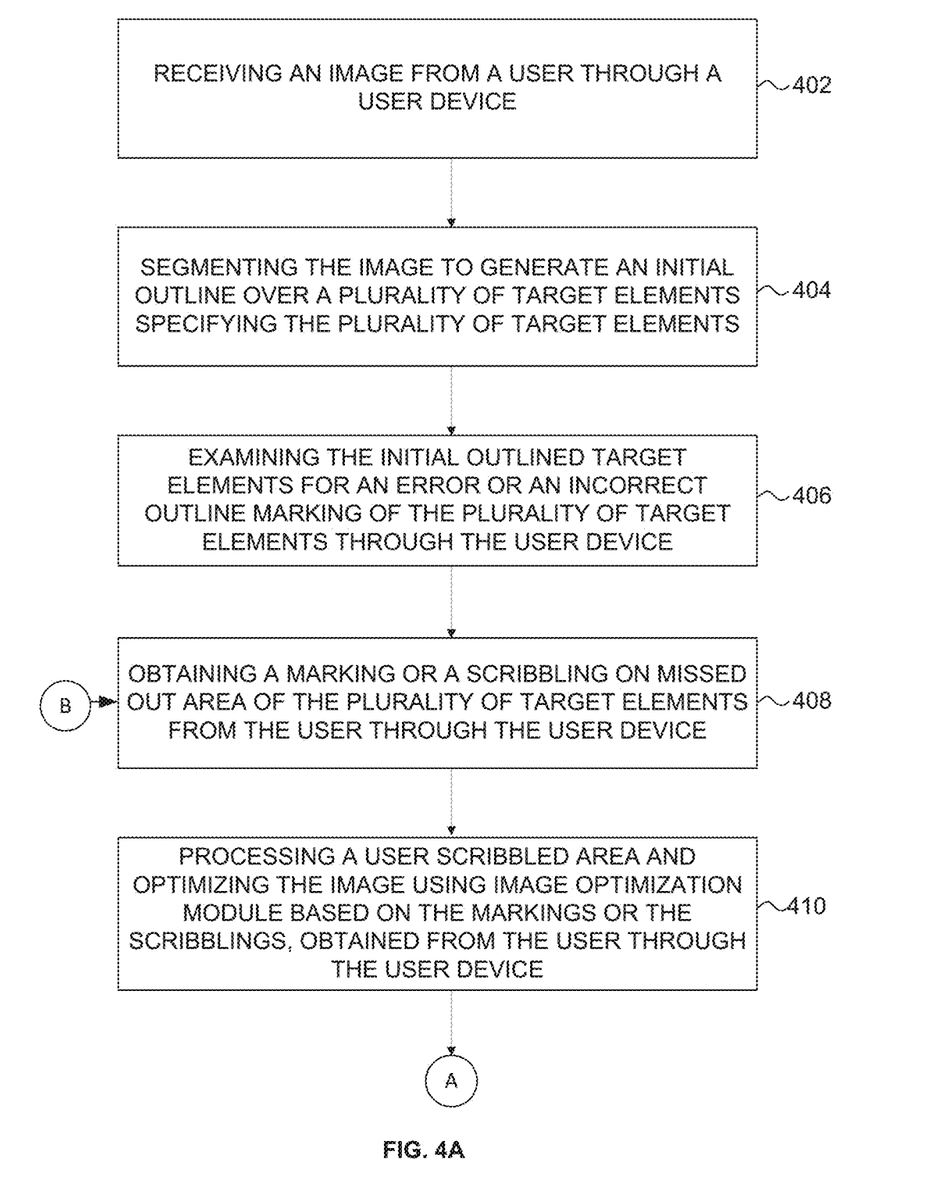
FIG. 4A is a flow diagram that illustrates a method of segmenting medical ages using a machine learning model, according to some embodiments herein.

FIG. 4A is a flow diagram that illustrates a method of segmenting medical images using a machine learning model, according to some embodiments herein. At step 402, the method includes, receiving an image from a user through a user device. At step 404, the method includes, segmenting the image to generate an initial outline on a plurality of target elements specifying the plurality of target elements. At step 406, the method includes, examining the initial outlined target elements for an error or an incorrect outline marking of the plurality of target elements through the user device. At step 408, the method includes, obtaining a marking or a scribbling on a missed-out area of the plurality of target elements from the user through the user device. At step 410, the method includes, processing a user scribbled area and optimizing the image using an image optimization module based on the markings or the scribblings, obtained from the user through the user device.

Figure 4B:
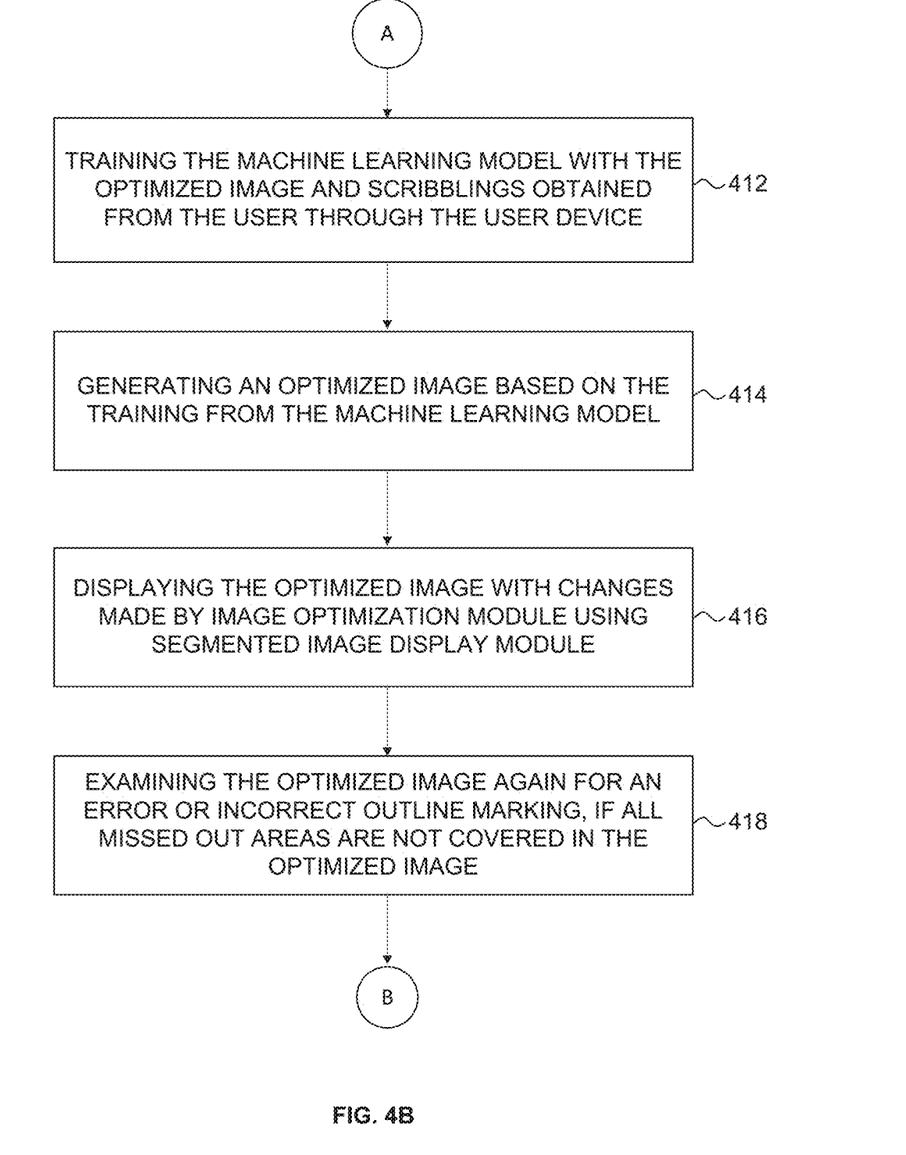
FIG. 4B is a flow diagram that illustrates a method for generating a scribble-based segmentation for medical imaging using a machine learning model, according to some embodiments herein.

FIG. 4B is a flow diagram that illustrates a method for generating a scribble-based segmentation for medical imaging using a machine learning model, according to some embodiments herein. At step 412, the method includes, training the machine learning model with the optimized image and scribblings obtained from the user through the user device. At step 414, the method includes, generating an optimized image based on the training from the machine learning model. At step 416, the method includes, displaying the obtained optimized image with changes made by image optimization module using segmented image display module. At step 418, the method includes, examining the optimized image again for an error or incorrect outline marking, if all missed out areas are not covered in the optimized image the process continues from the step 408.

Figure 5A:
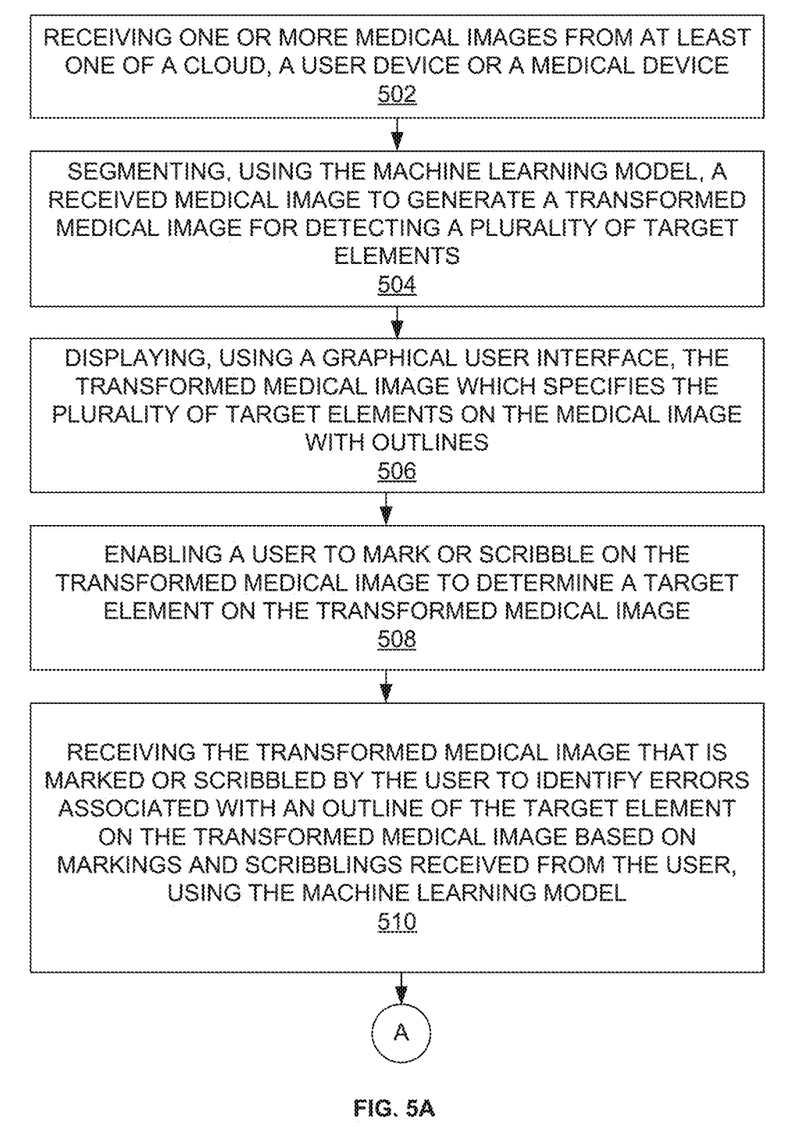
FIGS. 5A-5B are flow diagrams that illustrate a method for generating an optimized medical image using a machine learning model according to some embodiments herein.
Figure 5B:
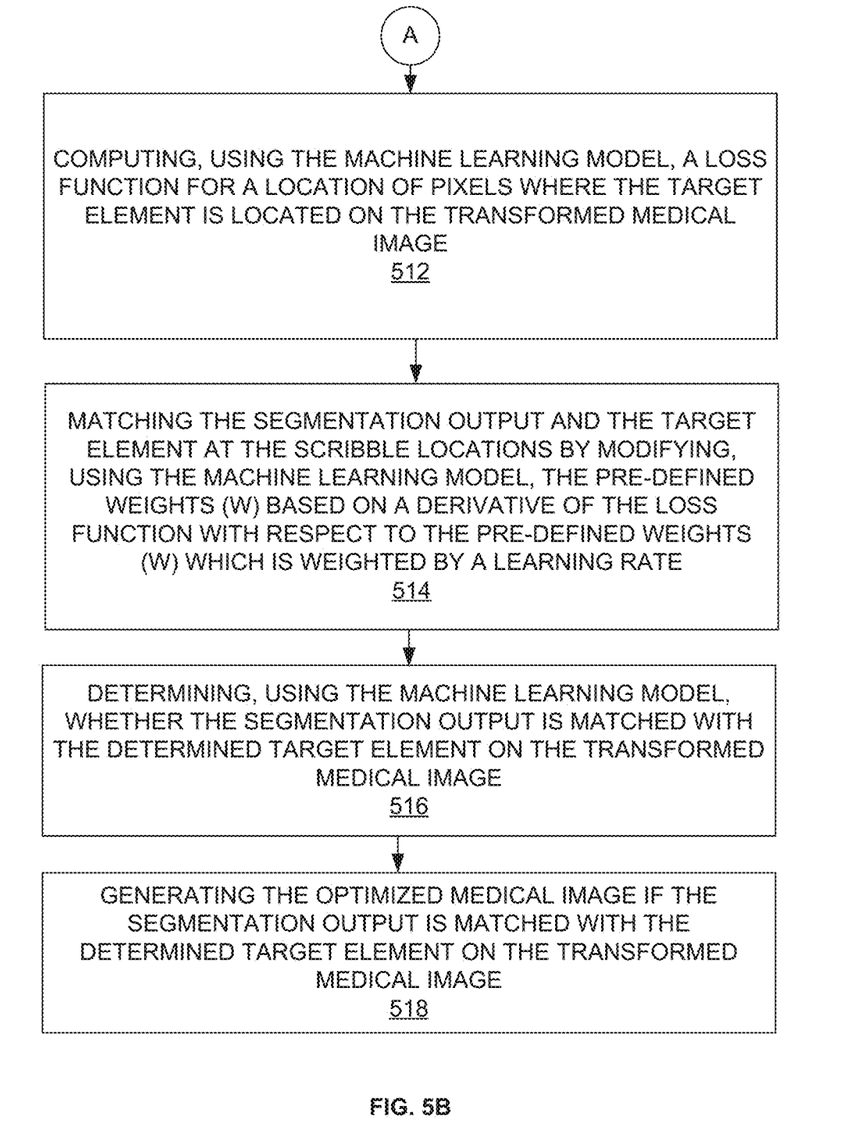

FIGS. 5A-5B are flow diagrams that illustrate a method for generating an optimized medical image using a machine learning model according to some embodiments herein. At step 502, one or more medical images from at least one of a cloud, a user device, or a medical device are received. At step 504, a received medical image is segmented to generate a transformed medical image for detecting a plurality of target elements using the machine learning model. The transformed medical image is a segmented output that is generated based on pre-defined weights (w). At step 506, the transformed medical image is displayed which specifies the plurality of target elements on the medical image with outlines. The transformed medical image is generated by the machine learning model that generates the outlines on the plurality of target elements. At step 508, a user is enabled to mark or scribble on the transformed medical image to determine a target element on the transformed medical image. At step 510, the transformed medical image that is marked or scribbled by the user is received to identify errors associated with an outline of the target element on the transformed medical image based on markings and scribblings received from the user using the machine learning model. At step 512, a loss function is computed for a location of pixels where the target element is located on the transformed medical image. At step 514, the segmentation output and the target element are matched at the scribble locations by modifying, using the machine learning model, the pre-defined weights (w) based on a derivative of the loss function with respect to the pre-defined weights (w) which is weighted by a learning rate. The learning rate determines a speed of change the pre-defined weights. At step 516, determined that the segmentation output whether matched with the target element on the transformed medical image. At step 518, the optimized medical image is generated if the segmentation output is matched with the target element on the transformed medical image. In some embodiments, the response received from the user includes scribblings or markings made on the transformed medical image.

The embodiments herein may include a computer program product configured to include a pre-configured set of instructions, which when performed, can result in actions as stated in conjunction with the methods described above. In an example, the pre-configured set of instructions can be stored on a tangible non-transitory computer-readable medium or a program storage device. In an example, the tangible non-transitory computer-readable medium can be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon.

Generally, program modules utilized herein include routines, programs, components, data structures, objects, and the functions inherent in the design of special-purpose processors, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps. The embodiments herein can include both hardware and software elements. The embodiments that are implemented in software include but are not limited to, firmware, resident software, microcode, etc. A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 6:
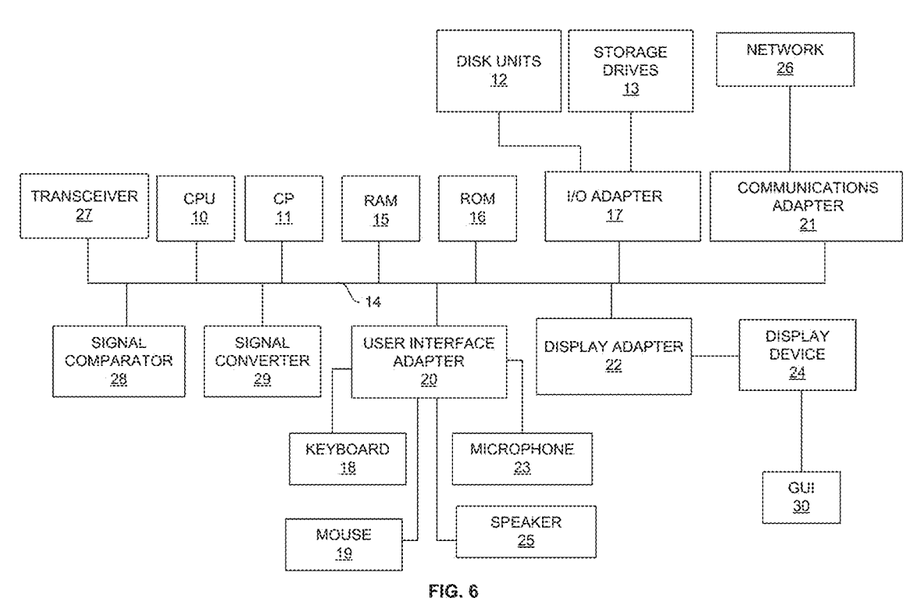
FIG. 6 is a schematic diagram of a computer architecture in accordance with the embodiments herein.

A representative hardware environment for practicing the embodiments herein is depicted in FIG. 6, with reference to FIGS. 1 through 5B. This schematic drawing illustrates a hardware configuration of a server 106/a computer system/a user device 102 in accordance with the embodiments herein. The user device 102 includes at least one processing device 10 and a cryptographic processor 11. The special-purpose CPU 10 and the cryptographic processor (CP) 11 may be interconnected via system bus 14 to various devices such as a random access memory (RAM) 15, read-only memory (ROM) 16, and an input/output (I/O) adapter 17. The I/O adapter 17 can connect to peripheral devices, such as disk units 12 and tape drives 13, or other program storage devices that are readable by the system. The user device 102 can read the inventive instructions on the program storage devices and follow these instructions to execute the methodology of the embodiments herein. The user device 102 further includes a user interface adapter 20 that connects a keyboard 18, mouse 19, speaker 25, microphone 23, and/or other user interface devices such as a touch screen device (not shown) to the bus 14 to gather user input. Additionally, a communication adapter 21 connects the bus 14 to a data processing network 26, and a display adapter 22 connects the bus 14 to a display device 24, which provides a graphical user interface (GUI) 30 of the output data in accordance with the embodiments herein, or which may be embodied as an output device such as a monitor, printer, or transmitter, for example. Further, a transceiver 27, a signal comparator 28, and a signal converter 29 may be connected with the bus 14 for processing, transmission, receipt, comparison, and conversion of electric or electronic signals.

The foregoing description of the specific embodiments will so fully reveal the general nature of the embodiments herein that others can, by applying current knowledge readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A system for generating an optimized medical image using a machine learning model, the system comprising:
   a memory;
   a processor that is configured to
      receive one or more medical images from at least one of a cloud, a user device or a medical device;
      segment, using the machine learning model, a received medical image to generate a transformed medical image for detecting a plurality of target elements, wherein the transformed medical image is a segmented output that is generated based on pre-defined weights (w);
      display, using a graphical user interface, the transformed medical image which specifies the plurality of target elements on the medical image with outlines, wherein the transformed medical image is generated by the machine learning model that generates the outlines on the plurality of target elements;
      enable a user to mark or scribble on the transformed medical image to determine a target element on the transformed medical image;
      receive the transformed medical image that is marked or scribbled by the user to identify errors associated with an outline of the target element on the transformed medical image based on markings or scribblings received from the user, using the machine learning model;
      compute, using the machine learning model, a loss function for a location of pixels where the target element is located on the transformed medical image;
      match the segmentation output and the target element at the mark or scribble locations by modifying, using the machine learning model, the pre-defined weights (w) based on a derivative of the loss function with respect to the pre-defined weights (w) which is weighted by a learning rate, wherein the learning rate determines a speed of change of the pre-defined weights;
      determine, using the machine learning model, whether the segmentation output is matched with the target element on the transformed medical image; and
      generate the optimized medical image if the segmentation output is matched with the target element on the transformed medical image.

2. The system of claim 1, wherein the pre-defined weights (w) are modified to reduce a value of the loss function, wherein the value of the loss function is decreased when the segmentation output is matched with the target element at the mark or scribble locations, wherein the value of the loss function is increased when the segmentation output is not matched with the target element at the mark or scribble locations.

3. The system of claim 1, wherein the system comprises a stochastic gradient descent process that modifies the pre-defined weights (w) optimally to reduce the loss function, wherein the derivative of the loss function is computed with respect to the pre-defined weights (w), wherein the pre-defined weights (w) are modified using a weighted multiplication of the learning rate and the derivative of the loss function.

4. The system of claim 1, wherein the processor is configured to receive the markings or scribblings from the user over a missed-out area of a plurality of detected elements from an initial outlined target element through a graphical user interface.

5. The system of claim 4, wherein the processor is configured to receive the markings or scribblings from the user over the missed-out area of the plurality of target elements determined from the optimized medical image using the graphical user interface and optimizes based on the markings or scribblings received from the user.

6. The system of claim 1, wherein the processor is configured to,
   provide optimized medical images and corresponding (i) pre-defined weights and (ii) markings and scribblings received from the user to the machine learning model as input data; and
   train the machine learning model using the input data to generate a trained machine learning model to generate the optimized medical image.

7. The system of claim 1, wherein the plurality of target elements comprises at least one of a cell, a ligament, a tissue, an organ, a tumor, a lesion, a part of bone, or an accessory bone.

8. A method for generating an optimized medical image using a machine learning model, the method comprising:
   receiving one or more medical images from at least one of a cloud, a user device, or a medical device;
   segmenting, using the machine learning model, a received medical image to generate a transformed medical image for detecting a plurality of target elements, wherein the transformed medical image is a segmented output that is generated based on predefined weights (w);
   displaying, using a graphical user interface, the transformed medical image which specifies the plurality of target elements on the medical image with outlines, wherein the transformed medical image is generated by the machine learning model that generates the outlines on the plurality of target elements;
   enabling a user to mark or scribble on the transformed medical image to determine a target element on the transformed medical image;
   receiving the transformed medical image that is marked or scribbled by the user to identify errors associated with an outline of the target element on the transformed medical image based on markings or scribblings received from the user, using the machine learning model;
   computing, using the machine learning model, a loss function for a location of pixels where the target element is located on the transformed medical image;
   matching the segmentation output and the target element at the mark or scribble locations by modifying, using the machine learning model, the pre-defined weights (w) based on a derivative of the loss function with respect to the pre-defined weights (w) which is weighted by a learning rate, wherein the learning rate determines a speed of change of the pre-defined weights;

determining, using the machine learning model, whether the segmentation matched with the target element on the transformed medical image; and generating the optimized medical image if the segmentation output is matched with the target element on the transformed medical image.

9. The method of claim 8, wherein the pre-defined weights (w) are modified to reduce a value of the loss function, wherein the value of the loss function is decreased when the segmentation output is matched with the target element at the mark or scribble locations, wherein the value of the loss function is increased when the segmentation output is not matched with the target element at the mark or scribble locations.

10. The method of claim 8, wherein the method comprises a stochastic gradient descent process, wherein the stochastic gradient descent process comprises, modifying the pre-defined weights (w) optimally to reduce the loss function, wherein the derivative of the loss function is computed with respect to the pre-defined weights (w), wherein the pre-defined weights (w) are modified using a weighted multiplication of the learning rate and the derivative of the loss function.

11. The method of claim 8, wherein the method comprises receiving the markings or scribblings from the user over a missed-out area of a plurality of detected elements from an initial outlined target element through a graphical user interface.

12. The method of claim 11, wherein the method comprises receiving the markings or scribblings from the user over the missed-out area of the plurality of target elements determined from the optimized medical image using the graphical user interface and optimizes based on the markings or scribblings received from the user.

13. The method of claim 8, wherein the method comprises providing optimized medical images and corresponding (i) pre-defined weights and (ii) markings and scribblings received from the user to the machine learning model as input data; and training the machine learning model using the input data to generate a trained machine learning model to generate the optimized medical image.

14. A non-transitory program storage device readable by a computer, and comprising a program of instructions executable by the computer to perform a method for generating an optimized medical image: using a machine learning model, the method comprising:

receiving one or more medical images from at least one of a cloud, a user device, or a medical device;

segmenting, using the machine learning model, a received medical image to generate a transformed medical image for detecting a plurality of target elements, wherein the transformed medical image is a segmented output that is generated based on pre-defined weights (w);

displaying, using a graphical user interface, the transformed medical image which specifies the plurality of target elements on the medical image with outlines, wherein the transformed medical image is generated by the machine learning model that generates the outlines on the plurality of target elements;

enabling a user to mark or scribble on the transformed medical image to determine a target element on the transformed medical image;

receiving the transformed medical image that is marked or scribbled by the user to identify errors associated with an outline of the target element on the transformed medical image based on markings or scribblings received from the user, using the machine learning model;

computing, using the machine learning model, a loss function for a location of pixels where the target element is located on the transformed medical image;

matching the segmentation output and the target element at the mark or scribble locations by modifying, using the machine learning model, the pre-defined weights (w) based on a derivative of the loss function with respect to the pre-defined weights (w) which is weighted by a learning rate, wherein the learning rate determines a speed of change of the pre-defined weights;

determining, using the machine learning model, whether the segmentation output is matched with the target element on the transformed medical image; and generating the optimized medical image if the segmentation output is matched with the target element on the transformed medical image.

15. The non-transitory program storage device of claim 14, wherein the pre-defined weights (w) are modified to reduce a value of the loss function, wherein the value of the loss function is decreased when the segmentation output is matched with the target element at the mark or scribble locations, wherein the value of the loss function is increased when the segmentation output is not matched with the target element at the mark or scribble locations.

16. The non-transitory program storage device of claim 14, wherein the method comprises a stochastic gradient descent process, wherein the stochastic gradient descent process comprises, modifying the pre-defined weights (w) optimally to reduce the loss function, wherein the derivative of the loss function is computed with respect to the pre-defined weights (w), wherein the pre-defined weights (w) are modified using a weighted multiplication of the learning rate and the derivative of the loss function.

17. The non-transitory program storage device of claim 14, wherein the method comprises receiving the markings or scribblings from the user over a missed-out area of a plurality of detected elements from an initial outlined target element through a graphical user interface.

18. The non-transitory program storage device of claim 14, wherein the method comprises receiving the markings or scribblings from the user over the missed-out area of the plurality of target elements determined from the optimized medical image using the graphical user interface and optimizes based on the markings or scribblings received from the user.

19. The non-transitory program storage device of claim 14, wherein the method comprises providing optimized medical images and corresponding (i) pre-defined weights and (ii) markings and scribblings received from the user to the machine learning model as input data; and training the machine learning model using the input data to generate a trained machine learning model to generate the optimized medical image.

* * * * *